United States Patent [19]

Ohkawara et al.

[11] Patent Number: 4,675,236
[45] Date of Patent: Jun. 23, 1987

[54] MONO-CORE TYPE MICROCAPSULES AND PROCESS FOR PRODUCING THEM

[75] Inventors: Masaaki Ohkawara, Yokohama; Masayuki Miyahara, Tama; Yoshitaka Ono, Chiba, all of Japan

[73] Assignee: Ohkawara Kokohki Co., Ltd., Yokohama, Japan

[21] Appl. No.: 793,003

[22] Filed: Oct. 30, 1985

[30] Foreign Application Priority Data

Jan. 29, 1985 [JP] Japan .................. 60-13648

[51] Int. Cl.$^4$ ............... B01J 13/02; B32B 9/02
[52] U.S. Cl. .................. 428/402.24; 264/4.3; 264/4.4; 426/72; 426/92; 426/805; 427/213.31; 424/450; 424/498
[58] Field of Search ............... 264/4.3, 4.4; 428/402.24; 424/38; 427/213.31; 426/72, 92, 805

[56] References Cited

U.S. PATENT DOCUMENTS

| | | | |
|---|---|---|---|
| 2,875,130 | 2/1959 | Grass, Jr. et al. | 424/19 |
| 3,079,351 | 2/1963 | Staneslow et al. | 428/914 X |
| 3,146,167 | 8/1964 | Lantz, Jr. et al. | 424/19 |
| 4,102,806 | 7/1978 | Kondo et al. | 264/4.4 X |
| 4,568,559 | 2/1986 | Nuwayser et al. | 428/402.24 X |

Primary Examiner—Richard D. Lovering
Attorney, Agent, or Firm—Armstrong, Nikaido, Marmelstein & Kubovcik

[57] ABSTRACT

This microcapsules are mono-core type microcapsules with particle size from 5 μm to 5 mm on which waxes are coated as the layer on the surface of the particles and/or penetrated to the inside of the particles, in which said wax coating is prepared by once melting the wax particles over the surface of the core particles and then re-solidifying them.

The core material of the microcapsule undergoes less thermal degradation and can be formed with a dense and thin membrane profiling the surface layer thereof with a use of lesser amount of waxes.

7 Claims, 13 Drawing Figures

FIG. 1a
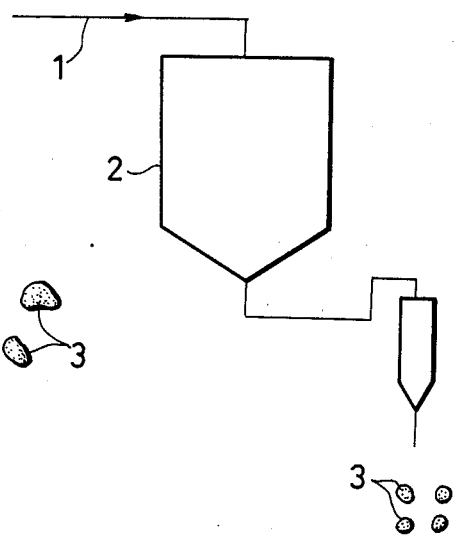
FIG. 1b
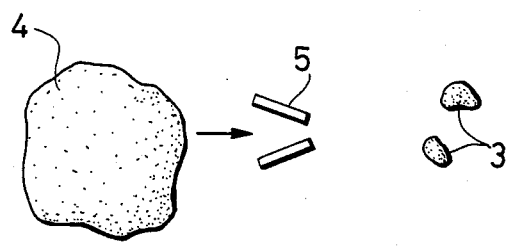
FIG. 2a    FIG. 2b
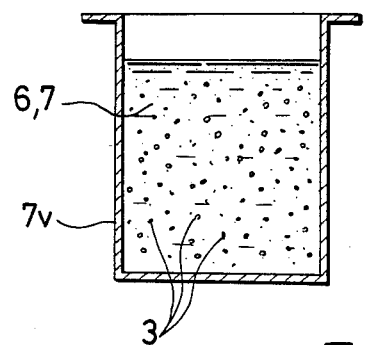 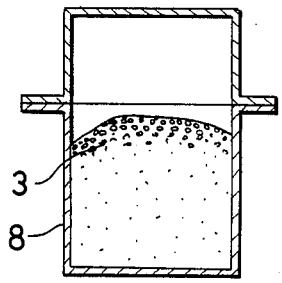
FIG. 2c
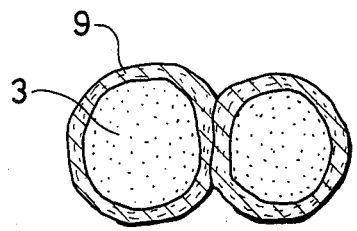

# MONO-CORE TYPE MICROCAPSULES AND PROCESS FOR PRODUCING THEM

BACKGROUND OF THE INVENTION

1. Field of the Invention

This invention concerns mono-core type microcapsules coated with waxes and a process for producing them.

Mono-core type microcapsules coated with waxes of this invention are utilized in all sort of industrial fields for medicines, foodstuffs, feeds, fertilizers, chemical products and the like.

2. Description of the Prior Art

Microcapsules have hitherto been produced by 14 types of methods as described in "Chemical Engineering of Japan", vol. 46, No. 10 (1982), on page 548.

These microcapsules are now utilized in all sort of industrial fuels for foodstuffs, medicines, agricultural agents, feeds, perfumes, enzymes, activated carbon and the like as described in the literature cited above. Among the 14 types of the production processes for the microcapsules aforementioned, aerial suspension process (fluidizing bed coating) and melt-dispersion-cooling process (spray and coagulating pelletization) have been known as typical examples for the method of depositing waxes to particles.

However, the former process, since the fluidizing bed is used in, particles as the core material are liable to be destroyed and no intact membranes can be formed because of the flaky shape of the membrane. Further, a great amount of waxes have to be used for forming the intact membrane.

Further, in the latter process, since the core material is added into the molten waxes, the core material is thermally denatured and a lot of waxes are required as well. Furthermore, the core material is localized in the wax or the core material is contained in the form of a plurality of particles in a wax particle to form multicored capsules. Accordingly, adequate microcapsule function can not be attained depending on the application uses, for example, in the case of fish feeds.

SUMMARY OF THE INVENTION

This invention provides mono-core type microcapsules coated with waxes and a process for producing them capable of overcoming the following problems in the conventional microcapsules as described below:

(a) The core material is destroyed.
(b) The core material is thermally denatured.
(c) A lot of wax is required.
(d) The core material forms a multi-cored and/or matrix structure or is localized in the wax.
(e) No dense and thin membrane can be formed on the surface of particles, if waxes are coated, in the case of using the fluidizing bed.

In order to overcome the foregoing problems in the prior art, this invention employs the following means.

(1) At first, fine particles less soluble in an organic solvent (hereinafter referred to as primary particle 3) are immersed in the organic solvent 7 containing waxes 6 dissolved therein.

(2) After immersing the primary particles into the wax solution of an organic solvent for a predetermined time, they are taken and vacuum-dried to form the primary wax membrane 9 thereon. The primary membrane 9 forms a coarse and not dense surface membrane, since the solvent is released, therethrough. Further, a portion of primary particles 3, 3 are agglomerated with each other by means of the dried primary membrane 9 into lumps.

(3) Then, lumped primary particles 3 are disintegrated into the assembly of the capsule semi-product 11 comprising mono-core type particles formed with the primary membrane 9 thereon.

(4) Then, since the capsule semi-product 11 is instantaneously melted and then quenched in a melting and quenching chamber 13, the coarse primary membrane 9 turns into the final membrane 16 which is highly smooth at the surface and in the shape profiling the surface layer of the particles.

Accodingly, the core material of the capsule product 17 undergoes less thermal degradation and can be formed with a dense and thin membrane profiling the surface layer thereof with a use of lesser amount of waxes.

BRIEF DESCRIPTION OF THE DRAWINGS

These and other objects, as well as features of this invention will now be described by way of preferred embodiments thereof while referring to the accompanying drawings, wherein FIG. 1(*a*) is an explanatory view for the step of forming the primary particles 3 by a spray dryer 2;

FIG. 1(*b*) is an explanatory view for the step of forming the primary particles 3 from dry lump starting material 4 by means of a crusher 5;

FIG. 2(*a*) is an explanatory view for the solution of waxes 6 in an organic solvent 7;

FIG. 2(*b*) is an explanatory view for the step of forming the primary membrane 9 on the primary particles 3;

FIG. 2(*c*) is an explanatory view for the lump of the primary particles 3 agglomerated by means of the primary membrane 9;

FIG. 3(*b*) is an explanatory view for the capsule semi-product 11;

FIG. 4(*b*) is an explanatory view for the microcapsule product 17;

DETAILED DESCRIPTION OF THE INVENTION

Figure 3A:
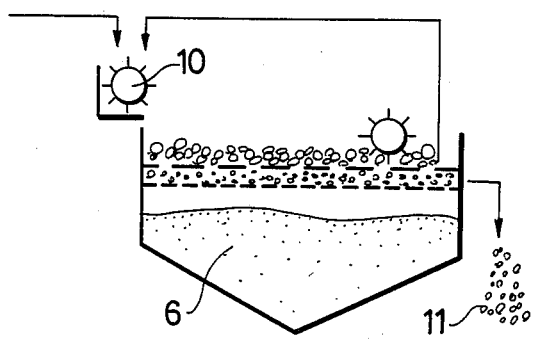
FIG. 3(*a*) is an explanatory view for the operation of an disintegrator 10.

This invention will now be described more in details.
Description for the Production Process (1) Preparation of primary particles:

As an embodiment, the starting material for the primary particles as the core material is supplied to a spray drier through a material feed pipe 1 in FIG. 1. The primary particle 3 can thus be formed by spray drying the starting material for the primary particles.

Examples of the materials and the properties of the primary particles 3 will be described later.

In another process for forming the primary particles 3, the primary particles 3 can also be obtained by preparing starting lump material 4 through drying in a dryer which are then pulverized in a crusher 5 as shown in FIG. 1(b).

(2) Preparation of primary wax membrane:

Waxes 6 are previously dissolved in an organic solvent 7 to prepare a wax solution which is stored in a container 7v as shown in FIG. 2(a). The concentration of the wax solution is generally from 0.01 to 40 wt %, preferably from 0.5 to 30 wt % and more preferably from 2 to 20 wt %. The primary particles 3 prepared as described above are immersed into the wax solution for 1–60 minutes as shown in FIG. 2(a).

Then, when the primary particles 3 are vacuum-dried. In this case, the vacuum degree is high at first and the final vacuum degree is generally 0.5 to 100 Torr, preferably 1 to 30 Torr and more preferably 1 to 10 Torr. The organic solvent 7 is evaporated from the solution containing the waxes at the surface of the primary particles 3 to form the primary membrane 9. It is of course necessary for the primary particles 3 that they are less soluble to the organic solvent 7 or should be surrounded with a less soluble substance.

Since the organic solvent 7 has been released through the primary membrane 9, the surface thereof becomes not dense but rough.

Further, a portion of the primary particles 3 is agglomerated with each other into a lump form due to the presence of the film-like primary membrane 9 as shown in FIG. 2(c).

Figure 3B:
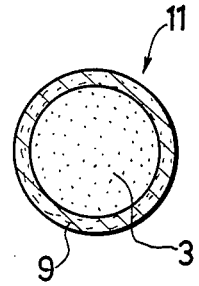

(3) Preparation of capsule semi-product 11:

The agglomerated particles are disintegrated in a disintegrator 10 as shown in FIG. 3(a) to obtain a capsule semi-product 11 formed with the primary membrane 9 as shown in FIG. 3(b).

It is desired for the waxes that they have such a crystalline structure as enabling this disintegration.

(4) Completion of microcapsule product:

The capsule semi-product 11 is supplied together with air (a) or nitrogen gas into a melting and cooling chamber 13. (FIG. 4)

Figure 4A:
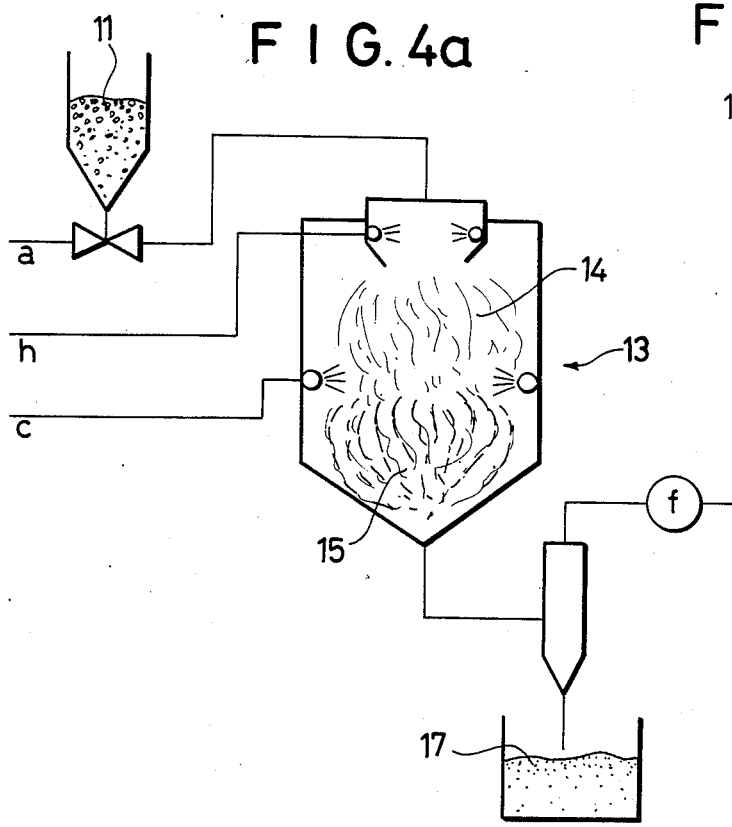
FIG. 4(*a*) is an explanatory view for the operation of the melting and cooling chamber.
Figure 4B:
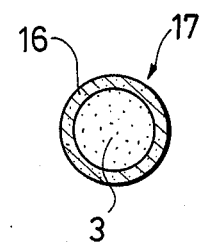

The primary membrane 9 on the semi-product particles 11 supplied into the melting and cooling chamber 13 is instantaneously melted in a hot gas zone 14 with a hot gas (h) at a temperature generally higher than the melting point by 30°–200° C., preferably by 50°–150° C. and more preferably by 75°–100° C., as shown in FIG. 4(a) Then, the molten primary membrane 9 is cooled to solidify again with a cold air (c) at a temperature below the melting point by 10–200° C., preferably by 30°–150° C. and more preferably by 50°–100° C., in the cooling zone 15. In this way, the final membrane 16 with a highly smooth surface and in a shape profiling the surface layer of particles is formed. The microcapsule product 17 can thus be produced in a short time continuously.

Waxes:

The waxes usable in this invention can include the followings.

1. Natural oil and fat and hardened oils:

Hardened, rapeseed oil, hardened castor oil, hardened beef tallow, palm oils, and the like.

2. Wax:

Carnauba wax, bleached bees wax, paraffin wax, montan wax, ceresine wax, candelilla wax, shellac wax, and the like.

3. Fatty acid ($C_{10}$ or higher)

Capric acid, undecanoic acid, lauryl acid, tridecyl acid, myristic acid, palmitic acid, stearic acid, elaidic acid, nonadecanoic acid, arachic acid, behenic acid, lignocerinic acid, octadecenoic acid, vaccenic acid, erucic acid, brassidic acid, cerotic acid, montanic acid, hexadecenic acid, eicosenic acid, pentadecylic acid, heptadecylic acid, heptacosanoic acid, melissic acid, racceric acid, lenolic acid, linolenic acid, undecylenic acid, cetoleic acid, arachidolinic acid, octadecylic acid, oleic acid, and the like.

4. Alcohols:

Undecanol, lauryl alcohol, tridecyl alcohol, myristyl alcohol, cetyl alcohol, stearyl alcohol, elaidic alcohol, nonadecyl alcohol, eicosyl alcohol, ceryl alcohol, pentadecyl alcohol, heptadecyl alcohol, melissyl alcohol, laccerol, undecyl alcohol, linoleyl alcohol, olein alcohol, linolenyl alcohol, and the like.

5. Fatty acid glycerine ester:

Caprin, myristine, palmistin, laurin, stearin, elaidin, brassidin, linolein, linolenin, olein, and the like.

6. Others: cholesteral, lecithin.

That is, waxes means those organic materials melted under heating and solidified by cooling as described above, either solely or in admixture.

It is desired that the waxes have such a crystalline structure as can be separated with no sticking upon disintegration in the disintegrator 10.

Organic solvent:

Organic solvent usable herein can include usual low boiling solvents such as ethanol, acetone, chloroform, carbon tetrachloride, benzene and n-hexane. Those solvents dissolving the primary particles 3 have to be avoided.

Examples of the material for the primary particle 3 and particle size of the microcapsules:

All sorts of materials, including both organic and inorganic materials, can be used as the primary particles 3. Examples of the organic material are shown in Examples (1) and (2). Examples of inorganic materials include ceramic particles, activated carbon and the like in addition to those shown in Example (3).

The microcapsules used herein are defined as those having particle size from 5 μm to 5 mm.

In the process according to this invention, since the primary membrane 9 is heat-melted instantaneously in the hot blow zone 14 and then quenched to re-solidify in the cooling zone 15, the particle size of the microcapsules is defined as within the above specified range. If the particles size is too small, the particles are suspended and not cooled immediately and, while on the other hand, if it is too large no uniform heat melting is possible.

Addition of water soluble material:

The collapsing time of the final film-like membrane 16 (or the release rate of core material) can be controlled by adding water soluble material to some extent to the waxes. Accordingly, it is desired to add water soluble material depending on the time required for using the microcapsules.

The water soluble material that can be added herein includes gelatin, gum arabic, sodium carboxymethylcellulose (CMC), polyvinyl alcohol (PVA), cellulose acetate phthalate (CAP), methyl methacrylic methacrylic acid copolymer (Eudragit L30D-55, trade name).

Figure 5:
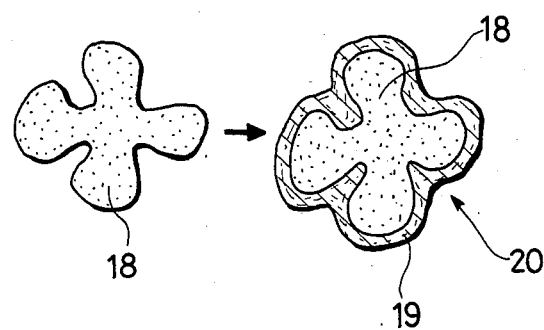
FIG. 5 shows another embodiment of the primary particles.

Other examples of primary particles:

As shown in FIG. 5, for instance, a porous material such as activated carbon is used as a core material carrier 18. The carrier is immersed in a solution containing the core material dissolved therein and adsorbed to penetrate and dried to form primary particles 20 carrying the core material 19 thereon.

The production step for the primary particles can thus be simplified. The primary particles using the carrier 18 is suitable for the catalyst or the like. In the case if the core material is soluble in the organic solvent, a primary particles less soluble to the organic solvent may be prepared by mixing a water soluble high molecular material, for example, sodium casein, skim milk powder and cyclodextrin.

EXAMPLE 1

This example shows the case where this invention is applied to fry young fish feeds.

(1) The following formulations are used for the fry young fish feeds.:
Egg yolk: 24 wt %
Shellfish (small clam) extracts: 8 wt %
Bonito extracts: 5 wt %
Egg albumin: 10 wt %
Cuttle liver oil: 2 wt %
Opossum shrimp (okiami) extract oil: 2 wt %
Vitamin E: 1 wt %
Oil and fat yeast: 12 wt %
Vitamin mixture: 8 wt %
Mineral mixture: 6 wt % were dissolved in water added to form an emulsion containing 40% solid component.

The emulsion was spray-dried using a spray drier to obtain particulates comprising primary particles of about 100 µm particle size.

(2) While on the other hand, 20 g of waxes comprising, 40% palmitic acid and 60% lauryl acid were dissolved in 80 g ethanol and kept at 40° C.

The particulates comprising the primary particles 3 were immersed for 5 minutes into the wax solution as described above.

(3) Then, the primary particle 3 were taken out from the wax solution and directly vacuum-dried. In this case, the vacuum degree was controlled to 10 Torr during the period while a great amount of the solvent was remained and to 2 Torr when the solvent was reduced to a smaller amount.

In this way, the primary membrane 9 was formed and, at the same time, the primary particles were agglomerated with each other by means of the primary membrane 9 into lumps.

(4) Then, the agglomerated primary particles 3 were disintegrated in a disintegrator 10 to obtain the assembly of capsule semi-product 11.

(5) Then, the assembly of the capsule semi-product 11 was supplied to a melting and cooling chamber 13 in which the primary membrane 9 was instantaneously melted at the hot gas zone 14 with a hot gas at a temperature of 200° C. and, thereafter, rapidly cooled to solidify in the cooling zone 15 with a cold gas at 20° C. to obtain microcapsule product 17 having the final membrane 16.

Figure 6:
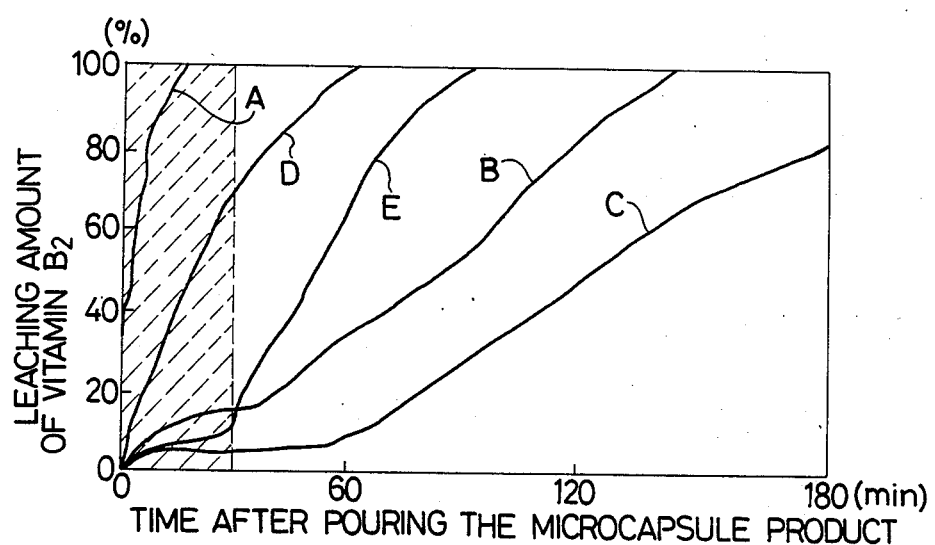
FIG. 6 is a graph showing the result of the test in Example 1.

The microcapsule product prepared as described above was poured into water and the leaching amount of vitamin $B_2$ contained therein was tested to obtain the curve B as shown in FIG. 6. In FIG. 6, the abscissa indicates the time after pouring the microcapsule product and the ordinate indicates the leaching amount of vitamin $B_2$.

In FIG. 6, the curve A shows the result of the test where no wax coating was applied at all.

Further, the curve (C) shows the result of the test carried out for the microcapsule product 17 obtained by immersing the primary particles 3 into a solution of 10 g of bleached bees wax as waxes dissolved in 90 g of chloroform.

The curve (D) shows the result for the test of the capsule product prepared by settling the formulation of the primary particles 3 as described above with a binder into fry young fish feeds.

The curve (E) shows the result of the test in a case where the water soluble material is added to the waxes shown by the curve (C). Addition of the water soluble material is attained by dispersing 5 g of fine powder prepared by spray drying Eudragit L-30D-55 into the chloroform solution containing bleached bees wax dissolved therein.

EXAMPLE 2

In this example, this invention was applied to medicines.

(1) Preparation of primary particles 3
100 g of a mixture comprising 70 wt % of sodium casein and 30 wt % of aspirin were dissolved into water incorporated with an emulsifier to obtain an emulsified suspension containing 20% solid component.

The emulsified liquid suspension was spray dried in a spray drier to obtain primary particles 3 with 50 µm average particle size.

(2) Wax solution
10 g of carnauba wax were dissolved in 90 g of chloroform and kept at 45° C.

(3) Immersion
The primary particles 3 as described above were immersed in the wax solution as described above for 5 minutes.

(4) Vacuum drying
The immersed primary particles 3 were taken out and directly vacuum-dried under 2 Torr of vacuum for one hour.

(5) Disintegration
The dried primary particles were disintegrated in the disintegrator 10 to form the assembly of the capsule semiproduct 17.

(6) Melting and cooling
The primary membrane 9 was instantaneously melted in the hot gas zone 14 (hot gas temperature at 180° C.) in the melting and cooling chamber 13 and, thereafter, quenched to solidify in the cooling zone 15 to obtain the microcapsule product 17.

Figure 7:
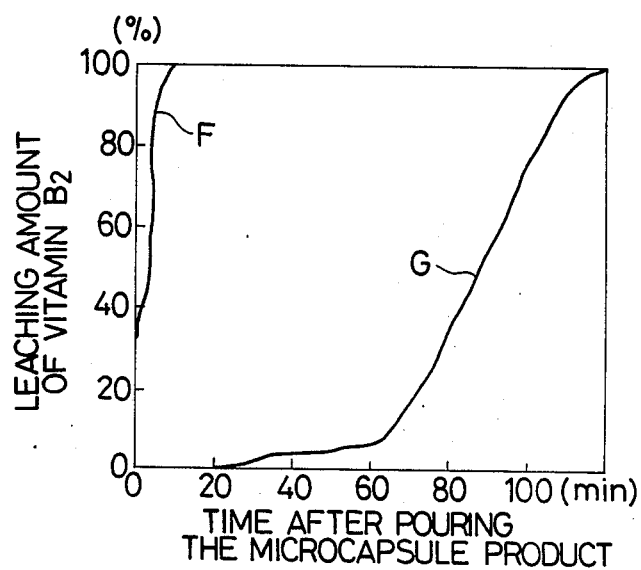
FIG. 7 is a graph showing the result of the test in Example 2.

(7) Test result
In FIG. 7, the curve (G) shows the result of the test for the microcapsule product 17 as described above and the curve (F) shows the result of the test for the aspirin powder not applied with the wax coating.

EXAMPLE 3

This example shows the case where this invention was applied to agricultural agents.

(1) Primary particle 3
Copper sulfate ($CuSO_4.5H_2O$) was dissolved in water and spray liquid with 40% solid contents was spray-dried in a spray drier to obtain particulates of 50 µm average particle size.

(2) Wax solution
5 g of carnauba wax were dissolved in 95 g of chloroform and kept at 40° C.

(3) Immersion

The primary particles 3 as described above were immersed in the wax solution as described above for 5 minutes.

(4) Vacuum drying

The primary particles 3 immersed as described above were instantly vacuum-dried for one hour under the vacuum degree of 2 Torr to form the lump product comprising particles formed with the primary membrane 9.

(5) Disintegration

The lump product was disintegrated to obtain the assembly of the capsule semi-product 11.

(6) Melting and cooling

The primary membrane 9 of the capsule semi-product 11 was instantaneously melted in the hot gas zone 14 with a hot gas at 180° C. Then, it was quenched to solidify in the cooling zone 15 with a cold gas at 15° C. to obtain the microcapsule 17.

(7) Test result

Figure 8:
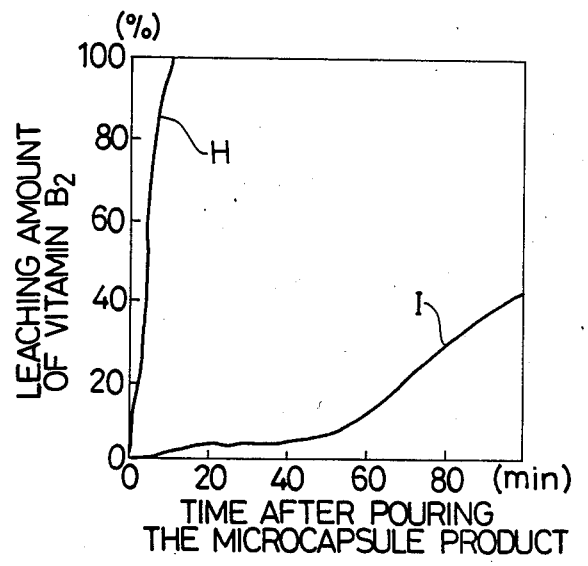
FIG. 8 is a graph showing the result of the test in Example 3.

In FIG. 8, the curve (I) shows the result of the test for the microcapsule products 17 and the curve (H) shows result of the test for those not applied with wax coating.

As mentioned above, this invention has the following advantages and effects.

(a) Since the microcapsules according to this invention undergo no impact shock during the production step therefor, different from the fluidizing layer coating process for instance, rhe primary particles 3 as the core material are free from damages.

(b) Since the capsule semi-product 11 is merely exposed to the high temperature only instantaneously and within a range not reaching the core material in the hot gas zone 14 of the melting and cooling chamber 13, the core material free from heat denaturation. This is extremely important in the case where the microcapsules according to this invention is served for such application uses where the core material has to be stored, for example, in foodstuffs, medicines and feeds.

(c) Since the final membrane 16 comprises the membrane with a highly smooth surface and in a shape profiling the surface layer of individual primary particles 3 and since a portion thereof penetrates to the inside of the core material, a satisfactory hydrophobic membrane can be obtained with a lesser amount of waxes.

(d) The strength of the membrane can be adjusted in the mono-core type microcapsules according to this invention by controlling the coating amount of the final membrane 16. In the conventional multi-cored capsules, the strength of the membrane can not be adjusted. For instance, in the case of using the microcapsules to the fry young fish feeds as in Example 1, adjustment for the strength of the membrane is necessary.

(e) Although the mono-core type particles may also be formed by using the fluidizing coating process, the particles thus formed show much scattering in the membrane strength and are inferior in the moisture proofness, fluidizing property, filling performance and handlability as compared with this invention.

(f) When fatty acid type waxes are used, microcapsules show good intra-intestinal solubility and can comply the requirements for the medicines.

What is claimed is:

1. Mono-core type microcapsules comprising particles of from 5 $\mu$m to 5 mm in size on which waxes being coated on at least surface of a core material, said waxes being coated at a temperature at which the cire material is not thermally denatured, said particles thereafter being dried to be roughly and not densely coated on the surface of the core material, after which the coated wax of the core material is heated instantaneously and thereafter quenched to be solidified, whereby a dense and smooth wax membrane is coated on the surface of the core material without heat denaturation of the core material.

2. A process for producing mono-core type microcapsules which comprises immersing primary particles of a particle size from 5 $\mu$m to 5 mm into a solution of waxes dissolved in an orgaic solvent, taking out and vacuum-drying the primary particles to form a primary wax membrane with a rough and not dense surface thereon, in which a portion of the primary particles is agglomerated by means of the layered membrane of the primary waxes, then disintegrating said agglomerated primary particles into the assembly of a capsule semi-product comprising mono-core type particles, then introducing said capsule semi-product to the hot gas zone to instantaneously melt the primary membrane and, thereafter, quenching to solidify said molten primary membrane in a cooling zone to obtain a mono-core type microcapsule product coated with a final membrane.

3. A process according to claim 2, wherein water soluble materials are added to the waxes.

4. A process according to claim 2, wherein the primary particles are vacuum-dried at a final vacuum of from 0.5 to 100 Torr.

5. A process according to claim 2, wherein the primary particles are vacuum-dried at a final vacuum of from 1 to 30 Torr.

6. A process according to claim 2, wherein a hot gas of a temperature higher than a melting point of the primary membrane by 30°-200° C. is introduced to the hot gas zone.

7. A process according to claim 2, wherein a cold gas of a temperature below the melting point of the primary membrane by 10°-200° C. is introduced to the cooling zone.

* * * * *

UNITED STATES PATENT AND TRADEMARK OFFICE
CERTIFICATE OF CORRECTION

PATENT NO. : 4,675,236

DATED : June 23, 1987

INVENTOR(S) : OHKAWARA et al

It is certified that error appears in the above-identified patent and that said Letters Patent is hereby corrected as shown below:

On the cover page, Item [73], "Ohkawara Kokohki Co., Ltd." should read --Ohkawara Kakohki Co., Ltd.--.

Signed and Sealed this

Nineteenth Day of April, 1988

Attest:

DONALD J. QUIGG

Attesting Officer

Commissioner of Patents and Trademarks